United States Patent [19]
Collins, II

[11] Patent Number: 5,979,072
[45] Date of Patent: Nov. 9, 1999

[54] EXTERNAL AUDITORY CANAL DRYING APPARATUS

[76] Inventor: Hamilton P. Collins, II, 42011 San Jose Dr., San Jacinto, Calif. 92583

[21] Appl. No.: 09/025,276

[22] Filed: Feb. 18, 1998

[51] Int. Cl.⁶ .................................................. F26B 19/00
[52] U.S. Cl. ............................. 34/90; 392/383; 128/746
[58] Field of Search ..................... 34/90, 96, 97, 34/98, 99, 100, 101; 392/379, 380, 383, 384, 385, 347, 360, 373, 374; 128/746, 748

[56] References Cited

U.S. PATENT DOCUMENTS

| | | | |
|---|---|---|---|
| 3,797,475 | 3/1974 | Hughes | 126/206 |
| 3,986,272 | 10/1976 | Feierabent | 34/97 |
| 4,206,556 | 6/1980 | Sabo et al. | 34/90 |
| 4,634,839 | 1/1987 | Gilbertson | 392/383 |
| 5,404,652 | 4/1995 | Sher | 34/90 |
| 5,555,637 | 9/1996 | Montagnino | 34/97 |
| 5,699,809 | 12/1997 | Combs et al. | 128/746 |

*Primary Examiner*—Henry Bennett
*Assistant Examiner*—Pamela A. Wilson
*Attorney, Agent, or Firm*—Henderson & Sturm

[57] ABSTRACT

An external ear canal drying apparatus 10 comprising a hinged clam shell style housing 11 containing a forced air generating unit 12 having a blower motor 25 and a heating element 26 operatively associated with an air intake and exhaust conduit 22 that has an exhaust port nozzle 24 dimensioned to receive a conduit 32 centrally disposed within a tapered resilient housing 31 having return air passageways 39 that surround the central conduit for introducing forced hot air into and out of the auditory canal 100.

17 Claims, 3 Drawing Sheets

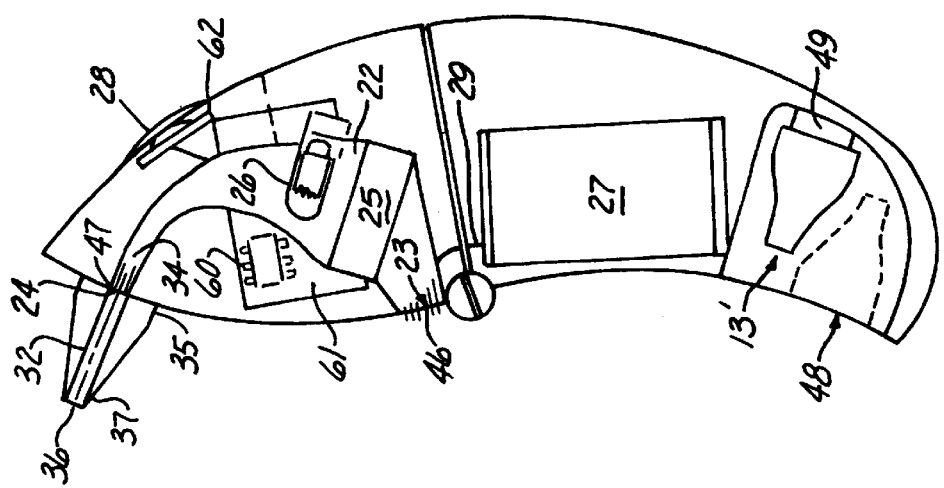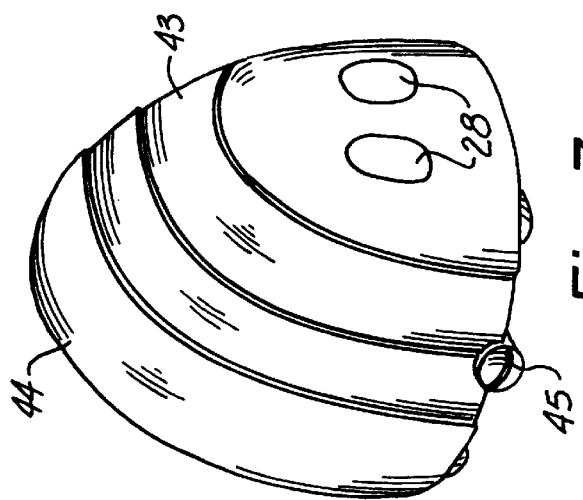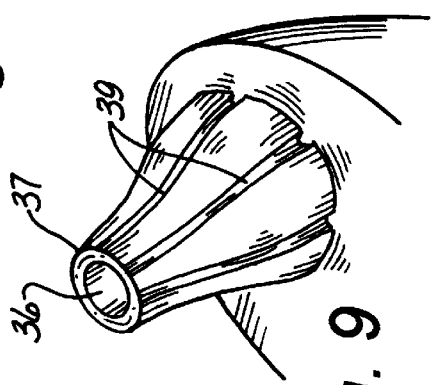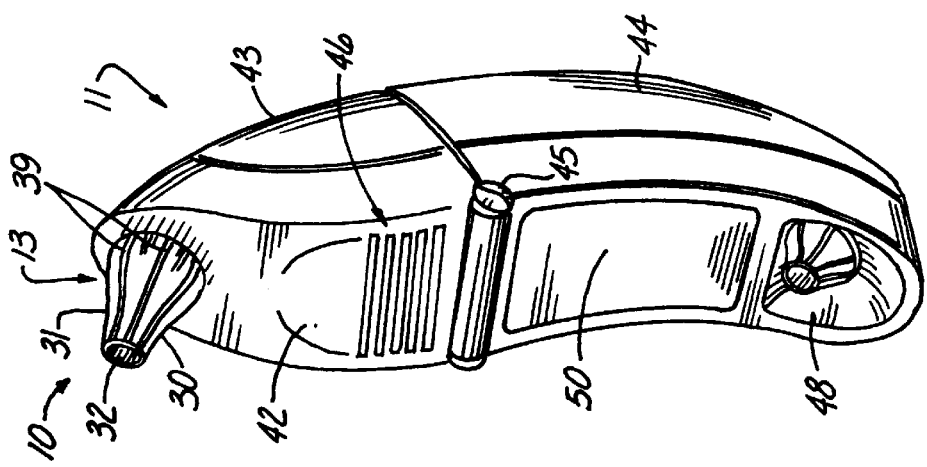

EXTERNAL AUDITORY CANAL DRYING APPARATUS

STATEMENT REGARDING FEDERALLY SPONSORED RESEARCH OR DEVELOPMENT

Not applicable.

CROSS REFERENCE TO RELATED APPLICATIONS

Not applicable.

REFERENCE TO MICROFICHE APPENDIX

Not applicable.

BACKGROUND OF THE INVENTION

1. Field of the Invention

The present invention relates to the field of medical implements in general, and in particular to a forced air device for removing moisture from a person's ear.

2. Description of Related Art

As can be seen by reference to the following U.S. Pat. Nos. 3,797,475; 3,986,272; 4,206,556; and 5,404,652, the prior art is replete with myriad and diverse forced air and other types of drying implements.

While all of the aforementioned prior art constructions are more than adequate for the basic purpose and function for which they have been specifically designed, they are uniformly deficient with respect to their failure to provide a simple, efficient and practical and safe way of removing moisture from a person's external ear canal.

As most physicians and otologists are all too well aware, there is not currently available an ear canal drying apparatus that can be used to remove moisture from a patient's ear canal which presents problems for those individuals having chronically moist and/or diseased ear canals, mastoid cavities, tympanic membrane perforations, user's of hearing aids and swimmers.

As a consequence of the foregoing situation, there has existed a longstanding need for a new and improved type of heated forced air device that is designed to introduce a flow of circulating air into a user's external ear canal to remove moisture from a person's external ear canal.

BRIEF SUMMARY OF THE INVENTION

Briefly stated, the external ear canal drying apparatus that forms the basis of the present invention comprises in general a housing unit, a forced air generating unit and a nozzle adapter unit that is removably received in the exhaust outlet of the forced air generating unit.

As will be explained in greater detail further on in the specification, the forced air generating unit includes an air inlet and exhaust conduit that is operatively associated with a blower motor and a heating element to deliver heated forced air through the exhaust port of the forced air generating unit.

In addition, the nozzle adapter unit includes a generally soft pliable tapered housing that is dimensioned to be partially received in a person's ear canal. In one version of the invention, the tapered housing is further provided with a suspended central conduit that delivers the heated air to the person's inner ear.

Furthermore, the central conduit also defines a concentric return passageway arranged within the tapered housing to allow the heated air to be vented from the person's ear canal. In another version of the invention, fluted recesses are formed on the exterior of the tapered housing wherein the heated air will escape through the recesses.

In the preferred embodiment of the invention, the housing unit comprises an upper and lower housing section which are hingedly connected to one another in a contoured clam shell fashion. The lower housing section is provided with a recess dimensioned to receive both the primary nozzle adapter unit and provide storage space for a spare nozzle adapter unit.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 6 is a perspective view of the preferred embodiment of the external auditory canal drying apparatus that forms the basis of the present invention disposed in the operative mode;

FIG. 7 is a perspective view of the preferred embodiment disposed in the storage mode;

FIG. 8 is a cross-sectional view taken through line 8—8 of FIG. 6; and

FIG. 9 is an isolated detail view of the external passage nozzle adapter unit.

DETAILED DESCRIPTION OF THE INVENTION

Figure 1:
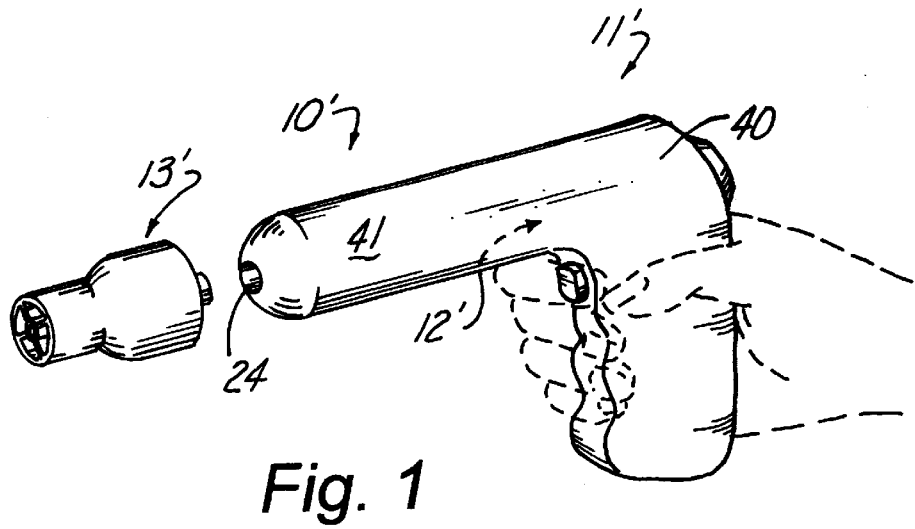
FIG. 1 is a perspective view of the alternate version of the external auditory canal drying apparatus that forms the basis of the present invention.

As can be seen by reference to the drawings, and in particularly to FIG. 1, the alternate version of the external auditory canal drying apparatus that forms a portion of the present invention is designated generally by the reference number 10'. The apparatus 10 comprises in general a housing unit 11', a forced air generating unit 12' and a nozzle adapter unit 13'. These units will now be described in seriatim fashion.

Figure 2:
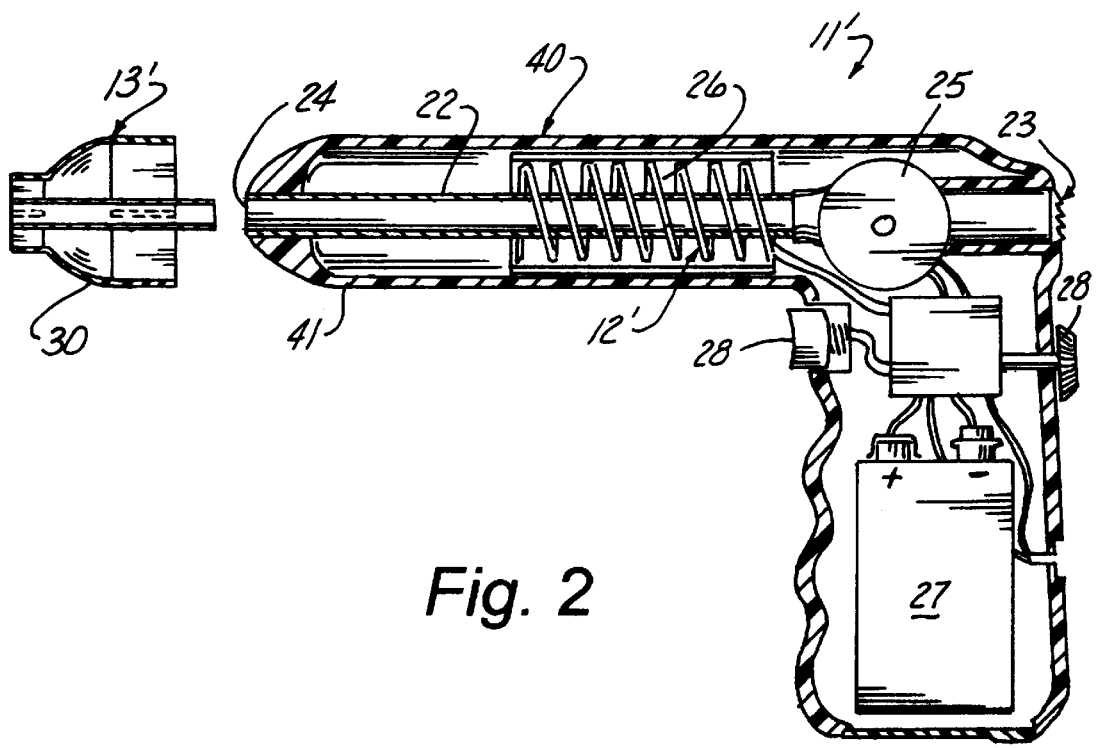
FIG. 2 is a cross sectional view of the alternate version of the ear canal drying apparatus.

As can best be seen by reference to FIG. 2, in the alternate version of the invention, the housing unit 11' comprises a hand held blower member 40, including a pistol shaped housing 41. The forced air generating unit 12' comprises an air intake and exhaust conduit 22 having an air intake port 23 disposed on one end of the housing 41 and an air exhaust port nozzle 24 which is disposed on the other end of the housing 41.

In addition, a blower motor 25 is disposed in line with the conduit 22 proximate the air intake port 23 and a heating element 26 is disposed in a surrounding relationship with the conduit 22 intermediate the blower motor 25 and the exhaust port nozzle 24. Heated forced air may be delivered to the exhaust port nozzle 24 in a well recognized fashion.

Furthermore, the forced air generating unit 12' is also provided with a power source 27 and a pair of switch elements 28, which selectively supply power to the blower motor 25 and the heating element 26, respectively.

At this juncture, it should be noted that given the sensitive nature of the human ear 100, both the air speed generated by the blower motor 25 and the air temperature generated by the heating element 26 must be maintained at fairly low values such that the air flow capacity of the blower motor 25 will not exceed 10 cc/sec. and the temperature of the heating element will not exceed 39° C. It should further be noted that the bower motor 25 must also have a very low decibel rating given its use in close proximity to a user's ear 100.

Figure 3:
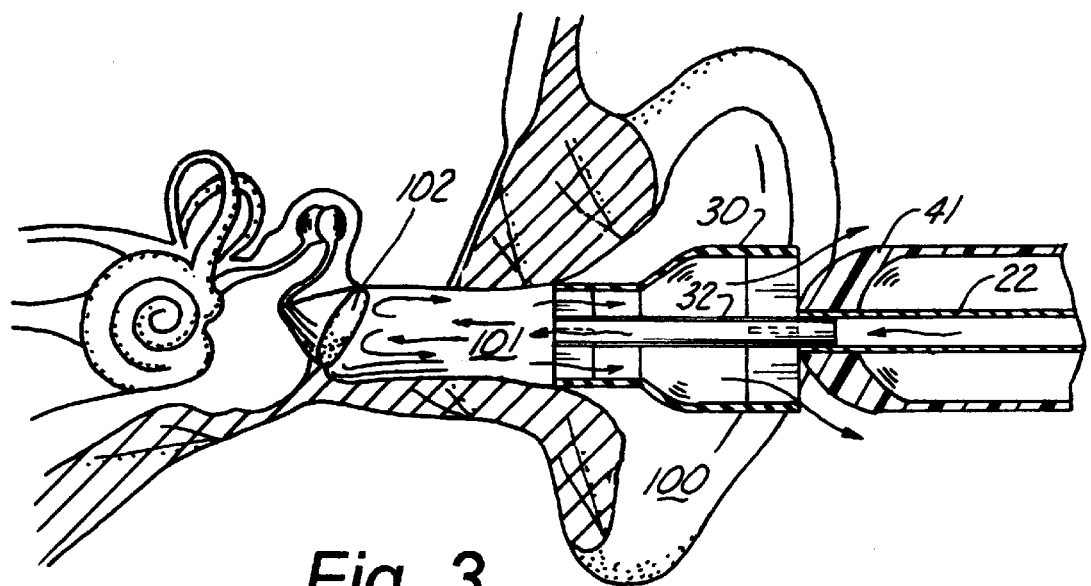
FIG. 3 is a detail view showing the interior passage nozzle adapter unit engaged in a person's ear.
Figure 4:
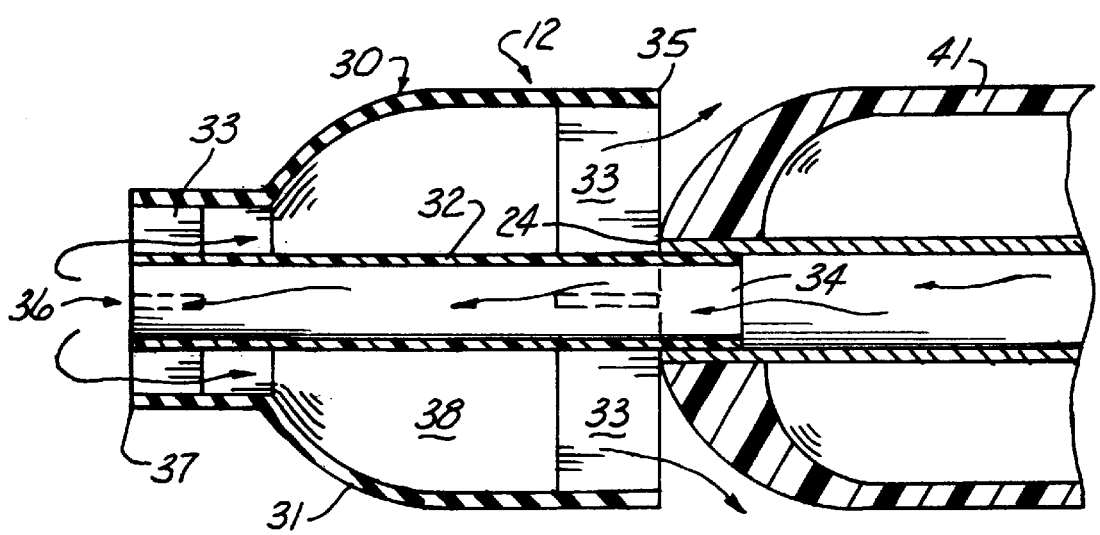
FIG. 4 is an isolated detail view of the engagement between the forced air generating unit and the interior passage nozzle adapter unit.
Figure 5:
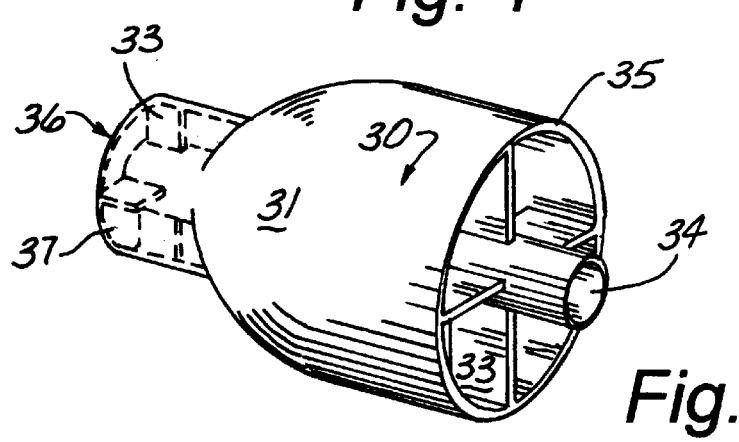
FIG. 5 is an isolated perspective view of the interior passage nozzle adapter unit.

Turning now to FIGS. 3 through 5, it can be seen that in the alternate version of the invention, the interior passage nozzle adapter unit 13' comprises a generally resilient adapter member 30 having a tapered housing 31 provided with a central conduit 32 which is suspended within the tapered housing 31 by a plurality of rib elements 33.

In addition, the central conduit 32 has an inlet port 34 which extends beyond the enlarged end 35 of the housing 31 and which is dimensioned to be frictionally engaged in the exhaust port nozzle 24 of the air intake and exhaust conduit 22 of the forced air generating unit 12'.

Furthermore, the central conduit 32 has an exhaust port 36 which is disposed within the narrow end 37 of the adapter member 30. As can best be seen by reference to FIG. 4, the central conduit 32 is spaced from the interior of the resilient tapered housing 31 to define an interior concentric return passageway 38 to allow the forced air to flow away from the person's ear drum 102.

It should also be noted that the tapered configuration of the resilient housing 31 is specifically designed to limit the extent of travel of the nozzle adapter unit 13' relative to the interior of the ear canal 101 and to space the exhaust port 36 and the narrow end 37 of the adapter member 30 from the user's ear drum 102.

Turning now to FIGS. 6 through 9, it can be seen that in the preferred embodiment of the invention the housing unit 11 includes a two-piece hinged housing member 42 having contoured upper 43 and lower 44 housing sections which are hingedly connected to one another as at 45 to produce a generally clam shell arrangement in the storage mode as depicted in FIG. 7.

In addition, as shown in FIGS. 6 and 8, the upper section 43 of the housing member 42 is provided with an air intake port opening 46 and an air exhaust port opening 47. The lower section 44 of the housing member 42 is provided with an enlarged recess 48 dimensioned to receive both the nozzle adapter unit 13 and a spare nozzle adapter 13 which is captively engaged on a tapered post element 49 disposed within the enlarged recess 48, and a battery access panel 50.

As can best be seen by reference to FIG. 8, the forced air generating unit 12 also comprises an air intake and exhaust conduit 22 having an air intake port 23 disposed on the lower portion of the upper housing section 43 and an air exhaust port nozzle 24 disposed on the outboard end of the upper housing section 43.

In addition, a fan or blower motor 25 is disposed in line with the conduit 22 and a heating element 26 such as a halogen bulb, or the like is disposed upstream of the blower motor 25 to deliver heated forced air to the exhaust port nozzle 24 in a well recognized fashion.

Furthermore, the forced air generating unit 12 includes a power source 27 such as a pair of batteries or the like disposed in the lower housing section 44. The power source 27 is electronically coupled to a control system 60 in the upper housing section 43 via electrical wiring 29.

Still referring to FIG. 8, it can be seen that the control system 60 comprises a circuit board 61, a pair of switches 28 that control the heating element 26 and the blower motor 25, respectively, and a temperature sensor 62 which is disposed intermediate the heating element 26 and the exhaust port nozzle 24 to limit the temperature of the heated air being generated by the apparatus 10 in a well recognized fashion.

As shown in FIGS. 6, 8, and 9, besides the distinctions between the housing units 11 and 11' and the location of the various components of the forced air generating units 12 and 12' in the preferred and alternate embodiments of this invention, the design and operation of the nozzle adapter units 13, 13' two embodiments are also somewhat distinctive.

In the preferred embodiment of the invention depicted in FIGS. 6, 8, and 9, the nozzle adapter unit 13 comprises a generally resilient adapter member 30 having a transparent tapered housing 31 provided with a central conduit 32. The central conduit 32 is provided with an inlet port 34 which extends beyond the enlarged end 35 of the tapered housing 31 and is dimensioned to be frictionally engaged in the exhaust port nozzle 24 of the forced air generating unit 12.

Furthermore, the central conduit 32 is provided with an exhaust port 36 which terminates in the narrow end 37 of the adapter member 30. The narrow end 37 of the adapter member 30 and the exhaust port 36 share a common juncture.

In addition, as can best be seen by reference to FIGS. 6 and 9, the external periphery of the tapered housing 31 is provided with a plurality of fluted recesses 39 which are designed to allow the heated air generated by the apparatus 10 to escape from the user's external auditory canal in a well recognized fashion.

Furthermore, since the tapered housing 31 is transparent, the user will be given a visual indication when the heating element 26 is in operation.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas, a screw employs a helical surface, in the environment of fastening wooden parts, a nail and a screw may be equivalent structures.

I claim:

1. An external auditory canal drying apparatus comprising:
   a housing unit including a housing member;
   a forced air generating unit disposed within the housing member and comprising an air intake and exhaust conduit having an air intake port on one end and an air exhaust port nozzle on the other end wherein the air intake and exhaust port is provided with a blower motor; and a nozzle adapter unit operatively associated with said exhaust port nozzle and including a generally resilient adapter member having a tapered housing provided with a central conduit for receiving a stream of forced air from said blower motor; and a return passageway disposed in a surrounding relationship relative to said central conduit for allowing the forced air to exit from the auditory canal.

2. The apparatus as in claim 1 wherein the air intake and exhaust conduit is further provided with a heating element.

3. The apparatus as in claim 2 wherein the tapered housing has an enlarged end disposed proximate to the exhaust port nozzle and a narrow end spaced from the exhaust port nozzle.

4. The apparatus as in claim 3 wherein the central conduit extends beyond the enlarge end of the tapered housing and is dimensioned to be received in said exhaust port nozzle.

5. The apparatus as in claim 3 wherein said return passageway is formed on the interior of the tapered housing.

6. The apparatus as in claim 3 wherein said return passageway is formed on the exterior of the tapered housing.

7. The apparatus as in claim 6 wherein said return passageway comprises a plurality of fluted recesses formed on the exterior of the tapered housing.

8. The apparatus as in claim 2 wherein said housing member has a generally pistol shaped configuration.

9. The apparatus as in claim 2 wherein said housing member has an upper housing section and a lower housing section hingedly connected to one another.

10. The apparatus as in claim 9 wherein said upper and lower housing sections are configured to form a clam shell configuration when joined together in the collapsed mode.

11. The apparatus as in claim 10 wherein the nozzle adapter unit is disposed on the upper housing section and the lower housing section is provided with a recess dimensioned to receive the nozzle adapter unit when the upper and lower housing sections are disposed in the collapsed mode.

12. The apparatus as in claim 11 wherein the recess in the lower housing section is further dimensioned to receive a spare nozzle adapter unit.

13. The apparatus as in claim 2 further comprising:

an electronic control system for governing the operation of the blower motor and the heating element.

14. The apparatus as in claim 13 wherein the control system limits the output of the blower motor to 10 cc/sec.

15. The apparatus as in claim 13 wherein the control system limits the temperature of the air heated by the heating element to 39° C.

16. The apparatus as in claim 2 wherein the tapered housing is dimensioned to only extend partially within the external auditory canal.

17. The apparatus as in claim 2 wherein the tapered housing is transparent.

* * * * *